(12) United States Patent
Insignares

(10) Patent No.: US 7,798,991 B2
(45) Date of Patent: Sep. 21, 2010

(54) TROCAR AND CANNULA ASSEMBLY HAVING VARIABLE OPENING SEALING GLAND AND RELATED METHODS

(75) Inventor: Rogelio A. Insignares, Miami, FL (US)

(73) Assignee: Genico, Inc., Winter Park, FL (US)

( * ) Notice: Subject to any disclaimer, the term of this patent is extended or adjusted under 35 U.S.C. 154(b) by 86 days.

(21) Appl. No.: 11/985,265

(22) Filed: Nov. 14, 2007

(65) Prior Publication Data
US 2008/0161758 A1    Jul. 3, 2008

Related U.S. Application Data

(60) Provisional application No. 60/865,824, filed on Nov. 14, 2006.

(51) Int. Cl.
*A61M 31/00*    (2006.01)

(52) U.S. Cl. ............... 604/93.01; 604/167.01; 604/167.02; 604/167.03; 604/167.04; 604/167.05; 604/167.06; 604/256; 604/165.01; 604/165.02

(58) Field of Classification Search ............... 600/181; 604/164.01, 165.01, 165.02, 167.01, 167.06, 604/256, 93.01; 606/167
See application file for complete search history.

(56) References Cited

U.S. PATENT DOCUMENTS

| | | | |
|---|---|---|---|
| 4,486,024 A | | 12/1984 | Cooper |
| 4,655,752 A | * | 4/1987 | Honkanen et al. ............ 604/256 |
| 4,960,412 A | * | 10/1990 | Fink ...................... 604/167.04 |
| 5,104,383 A | | 4/1992 | Shichman |
| 5,150,702 A | | 9/1992 | Miyanaga et al. |
| 5,209,737 A | | 5/1993 | Ritchart et al. |
| 5,226,891 A | | 7/1993 | Bushatz |
| 5,308,336 A | | 5/1994 | Hart |
| 5,342,315 A | * | 8/1994 | Rowe et al. ............ 604/167.06 |
| 5,376,077 A | | 12/1994 | Gomringer |
| 5,385,552 A | * | 1/1995 | Haber et al. ........... 604/167.03 |
| 5,385,553 A | | 1/1995 | Hart et al. |
| 5,411,483 A | | 5/1995 | Loomas et al. |
| 5,443,452 A | | 8/1995 | Hart et al. |

(Continued)

FOREIGN PATENT DOCUMENTS

EP    0066008 A1    12/1982

(Continued)

*Primary Examiner*—Nicholas D Lucchesi
*Assistant Examiner*—Scott Medway
(74) *Attorney, Agent, or Firm*—Innovative IP, PLC; Sandra M. Sovinski

(57) ABSTRACT

A trocar system for endoscopic surgery, cap assembly, and related methods are provided. The cap assembly includes a housing with an opening formed in line with an axis of the housing. The cap assembly also includes a variable opening flexible sealing gland having a stack of valve body sections each including a valve extension extending from a valve ring and having a valve opening and a slit extending between a valve opening and the valve ring. The combination of the individual valve body sections forms a substantially conically shaped iris diaphragm portion of the sealing gland. The iris is positioned to individually and separately receive elongate tools so that when any one of the elongate tools is positioned through the valve opening, a seal is maintained between peripheries of the seal gland surrounding the iris and outer peripheries of the inserted elongate tool.

10 Claims, 16 Drawing Sheets

U.S. PATENT DOCUMENTS

| | | |
|---|---|---|
| 5,449,141 A | 9/1995 | Gillett et al. |
| 5,576,792 A | 11/1996 | O'Brien et al. |
| 5,603,702 A * | 2/1997 | Smith et al. .................. 604/256 |
| 5,657,963 A | 8/1997 | Hinchliffe et al. |
| 5,782,812 A | 7/1998 | Hart et al. |
| 5,792,113 A | 8/1998 | Kramer et al. |
| 5,827,228 A | 10/1998 | Rowe |
| 5,895,377 A | 4/1999 | Smith et al. |
| 5,923,913 A | 7/1999 | O'Brien et al. |
| 5,989,224 A | 11/1999 | Exline et al. |
| RE36,702 E | 5/2000 | Green et al. |
| 6,551,282 B1 | 4/2003 | Exline et al. |
| 6,569,119 B1 | 5/2003 | Haberland et al. |
| 6,569,120 B1 * | 5/2003 | Green et al. ........... 604/167.04 |
| 6,632,200 B2 * | 10/2003 | Guo et al. .................... 604/247 |
| 6,702,787 B2 * | 3/2004 | Racenet et al. ............... 604/256 |
| 6,980,376 B2 | 12/2005 | Bamberger et al. |
| 7,025,747 B2 * | 4/2006 | Smith .................... 604/167.06 |
| 2003/0195472 A1 * | 10/2003 | Green et al. ........... 604/167.04 |
| 2004/0230161 A1 * | 11/2004 | Zeiner ................... 604/167.06 |
| 2005/0131349 A1 | 6/2005 | Albrecht et al. |
| 2005/0165433 A1 | 7/2005 | Haberland et al. |
| 2006/0027675 A1 | 2/2006 | Takeda |
| 2006/0047293 A1 | 3/2006 | Haberland et al. |
| 2006/0217665 A1 * | 9/2006 | Prosek .................. 604/167.02 |
| 2007/0185453 A1 * | 8/2007 | Michael et al. ......... 604/164.01 |

FOREIGN PATENT DOCUMENTS

| | | |
|---|---|---|
| EP | 0131349 A1 | 1/1985 |

\* cited by examiner

TROCAR AND CANNULA ASSEMBLY HAVING VARIABLE OPENING SEALING GLAND AND RELATED METHODS

CROSS-REFERENCE AND PRIORITY CLAIM TO RELATED APPLICATION

To the fullest extent permitted by law, the present U.S. Non-provisional patent application claims priority to and the benefit of U.S. Provisional patent application entitled "Trocar and Cannula Assembly Having Variable Opening Sealing Gland and Related Methods," filed on Nov. 14, 2006, on behalf of inventor Rogelio A. Insignares, and having assigned Ser. No. 60/865,824.

FIELD OF THE INVENTION

The present invention relates in general to the field of medical devices. More particularly, the present invention relates to trocar systems, cannulas, valves, and methods.

BACKGROUND OF THE INVENTION

Trocar systems have been developed over the years for various endoscopic applications in the field of medicine. These trocar systems conventionally include a cannula through which a trocar or obturator or other endoscopic related tool extends. It is known to use one or more valves positioned within or connected to a proximal end of the cannula of a trocar system. Examples of such trocar systems having one or more valves in the cannula thereof are known. These devices, however, can be bulky and awkward to use, have complex multi-component mechanical valves which can be difficult and expensive to manufacture, and can have an increased risk of mechanical failure. The mechanical valves also have little or no flexibility.

Other trocar systems have been developed which are easier to use and have less complex mechanical valves. One example of such trocar system can be seen in U.S. Pat. No. 6,569,119 by Haberland et al., entitled "Trocar System Having Cannula with Finger Grips," and other improvements can be seen in U.S. Patent Application publication no. 2006027675, entitled "Trocar and cannula assembly having conical valve and related methods," and publications nos. 20060047293 and 20050165433, both entitled "Trocar having planar fixed septum seal and related methods," and all by Haberland et al. These devices provide enhanced gripping and easier handling of the systems. Nevertheless, there is also still a need for alternative cannula and valve configurations for trocar systems, a need for relatively less expensive trocar systems, a need for trocar systems with better performance, and a need for more flexible trocar systems and valves which enhance handling thereof by medical personnel users, i.e., physicians, and yet are still effective for various endoscopic surgical procedures.

SUMMARY OF THE INVENTION

With the foregoing in mind, embodiments of the present invention advantageously provide embodiments of a valve having a unique design to provide a secured seal around a plurality of tools that individually and separately extend through the valve. Such embodiments of a valve provide an easier insertion and retraction of various laparoscopic surgical instruments, as well as other surgically related items which have varying diameters. Problematical instruments do not get obstructed or caught in a multi-component valve assembly as disclosed in the prior art. Embodiments of the present invention also advantageously provide a trocar system having relatively low costs associated with the manufacturing of components of the system, e.g., valves, and thereby can reduce the cost associated with the trocar system. Embodiments of the present invention additionally advantageously provide a more flexible trocar system which is effective during various endoscopic surgical procedures. Embodiments of the present invention further advantageously provide enhanced methods of forming a seal around tools and of using a trocar system during surgical procedures. Still further, because embodiments of a valve can have a relatively flat and thin profile and because peripheries of a valve are fixedly connected to a valve housing, the valve advantageously can operate like a membrane. Furthermore, because various types and diameters of tools can be used by medical personnel, embodiments of a valve advantageously allow one type of valve, cannula, or trocar system to be readily used for all of these various sizes and types of tools.

As previously described, a trocar system includes, but is not limited to, a cannula having an elongate cannula body with medial and distal portions. Such a trocar system also includes a valve housing being readily detachably connected to the proximal portion of the cannula body with such valve housing having an axis and a first opening at a proximal end of the valve housing, a second opening at a distal end of the valve housing, and an axially downward facing shoulder. Such a trocar system also includes a cap assembly which includes at least one valve positioned entirely within the valve housing. Such an at least one valve can include a valve body having an annular-shaped valve opening positioned in a medial portion of the valve body and adapted to individually and separately receive a plurality of different elongate tools. Each of the tools has a different diameter therethrough so that when any one of the plurality of elongate tools is positioned through the valve opening, a septum seal is maintained between peripheries of the valve body surrounding the valve opening and abuttingly contacting outer peripheries of the any one of the plurality of elongate tools extending therethrough.

Such a valve body has first and second layers of a fabric material and a layer of elastomeric material positioned between and contacting each of the first and second layers of the fabric material, and also has a periphery valve section connected to and extending radially outwardly from peripheries of the valve body, wherein the periphery valve section includes an outer ring, with an outer perimeter thereof defining an outer perimeter of the septum valve, the outer ring engaging the axially downward facing shoulder of the valve housing. The periphery valve section has a plurality of rib members, each radially extending substantially an entire distance between an outer perimeter of the valve body and the outer perimeter of the periphery valve section, and symmetrically positioned spaced-apart from each other. The periphery valve section has a greater flexibility than the valve body. The trocar system also includes a compression ring positioned in the valve housing adjacent the septum valve. The compression ring compresses the outer ring of the septum valve against the axially downward facing shoulder of the valve housing in order to fixedly position the septum valve within the valve housing. The compression ring has a compression ring opening substantially aligned, axially, with the first opening of the valve housing.

Further, the cap assembly of such a trocar system can include, but is not limited to, a valve housing having at least one opening formed in line with an axis of the valve housing, with the at least one opening being defined by a plurality of sidewalls extending in a substantially axial direction. The cap assembly also includes at least one valve positioned adjacent to the at least one opening of the valve housing. The at least one valve includes a valve body having an annular-shaped valve opening adapted to individually and separately receive a plurality of different elongate tools. Each of the elongate tools can have a different diameter so that when any one of the plurality of elongate tools is positioned through the valve opening and abuttingly contacting outer peripheries of the any one of the plurality of elongate tools extending therethrough, a septum seal is maintained between peripheries of the valve body surrounding the valve opening. The valve body has at least one layer of a fabric material and a layer of elastomeric material. The valve body also has a periphery valve section connected to and extending radially outwardly from peripheries of the valve body. The periphery valve section has a plurality of rib members, each radially extending substantially an entire distance between an outer perimeter of the valve body and an outer perimeter of the periphery valve section.

Accordingly, embodiments of the present invention include a cap assembly of an endoscopic cannula. The cap assembly can include a sealing gland housing having at least one opening formed in line with an axis of the sealing gland housing, the at least one opening being defined by an inner sealing gland housing sidewall. The cap assembly can also include a sealing gland positioned at least partially within the sealing gland housing and including a valve body including a plurality of valve body sections each having a first valve section including an annular shaped valve ring, and a second valve section extending from the first valve section and including a valve extension having a proximal end portion, a distal end portion, and a substantially conically shaped medial portion connected to and extending therebetween. A valve opening is positioned in the distal end portion of the valve extension and is adapted to receive therethrough an elongate tool. A slit extends between the valve opening and the valve ring. Each one of the valve rings of each of the plurality of valve body sections abuttingly contacts at least two other of the valve rings of the plurality of valve body sections to form a layered cap assembly valve ring. Additionally, the medial portion of the valve extension of each one of the plurality of valve body sections slidably contacts the medial portion of the valve extension of at least two other of the plurality of valve body sections. The combination of the plurality of valve body sections form an interweaved cap assembly valve extension.

Embodiments of the present invention also include a method of forming a sealing gland for a cap assembly of a cannula. For example, according to an embodiment of the present invention, the method can include forming a plurality of valve body sections, each having a first valve section including an annular shaped valve ring, a second valve section extending from the first valve section and including a valve extension having a proximal end portion, a distal end portion, and a substantially conically shaped medial portion connected to and extending therebetween. A valve opening can be positioned in the distal end portion of the valve extension and is adapted to receive an elongate tool therethrough. The method also includes forming a slit in the each of the plurality of valve body sections, extending between the respective valve opening and the respective valve ring, and positioning each one of the valve rings of each of the valve body sections in abutting contact with the other valve rings to form a layered cap assembly valve ring. The medial portion of the valve extension of each one of the valve body sections slidably contacting the medial portion of the valve extension of the other valve body sections to form an interweaved cap assembly valve extension. The combination of the valve body sections form the sealing gland.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

DETAILED DESCRIPTION OF THE INVENTION

The present invention will now be described more fully hereinafter with reference to the accompanying drawings, which illustrate embodiments of the invention. This invention may, however, be embodied in many different forms and should not be construed as limited to the illustrated embodiments set faith herein. Rather, these embodiments are provided so that this disclosure will be thorough and complete, and will fully convey the scope of the invention to those skilled in the art. Like numbers refer to like elements throughout, the prime or double prime notation, if used, indicates similar elements in alternative embodiments.

For clarity and simplicity, because the improvements and inventive elements presented herein, such as and without limitation opening flexible valve or sealing gland 250, 250', are operatively related and configured for preferred utilization with exemplary trocar system 120, as shown in FIGS. 1-10, a brief description of trocar system 120 follows, whereafter components common to previously described trocar system 120, such as cannula 40, and the improvements and inventive elements presented herein, will retain their original numbering. Those components not common will be renumbered accordingly.

Figure 1:
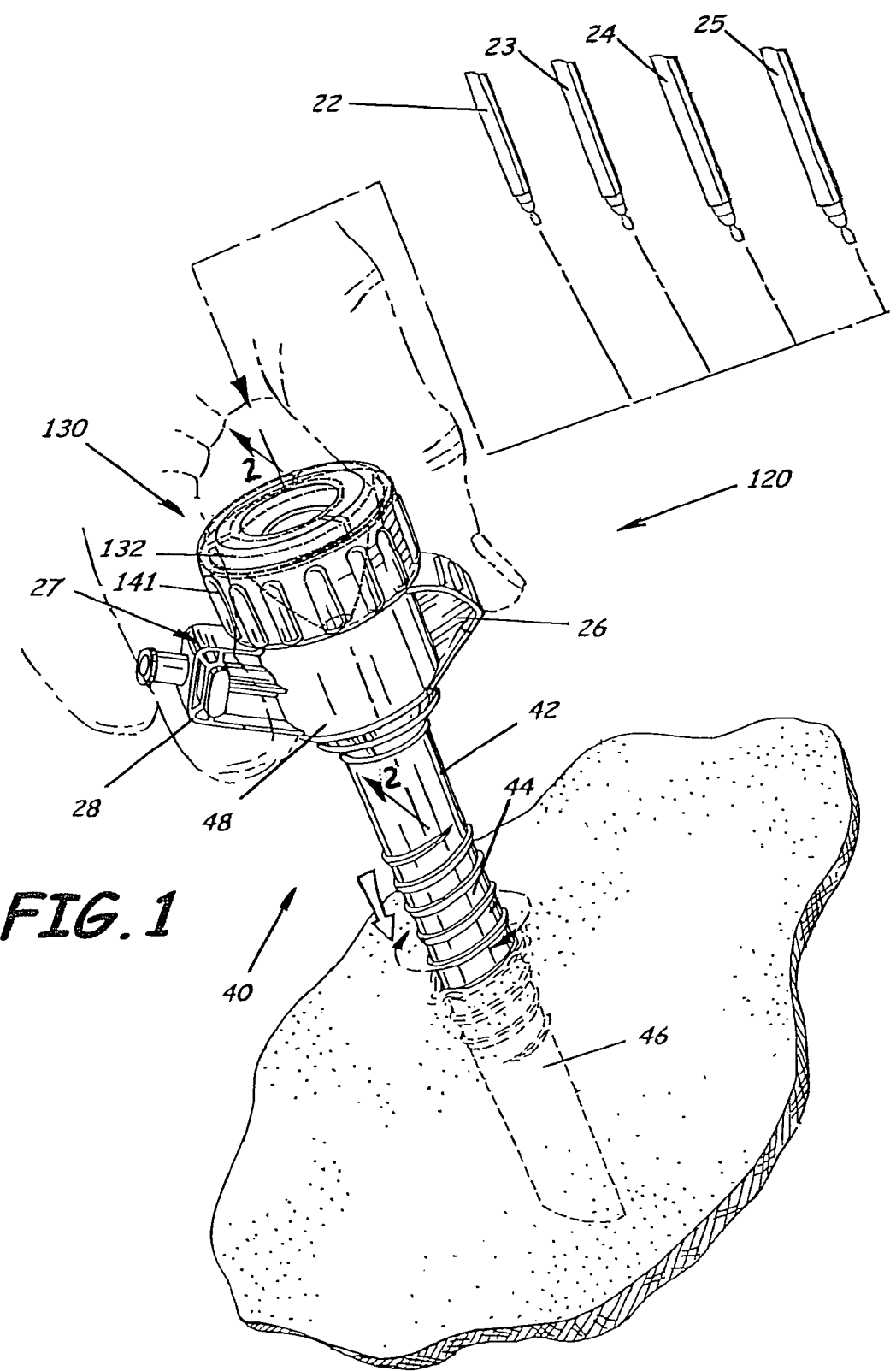
FIG. 1 is a perspective environmental view of an exemplary trocar system positioned within a layer of epidermis of a patient.

Previously described trocar system 120 employs a nonplanar valve 150 which can be used with the cannula 40. As illustrated in FIG. 1, exemplary trocar system 120 includes a plurality of tools 22, 23, 24, 25, each having an elongate body for extending through cap assembly 130 and cannula 40, and each having a different diameter in the range of from about 4 millimeters to about 13 millimeters. The tools can be obturators or other endoscopic related tools for various endoscopic procedures.

Figure 2:
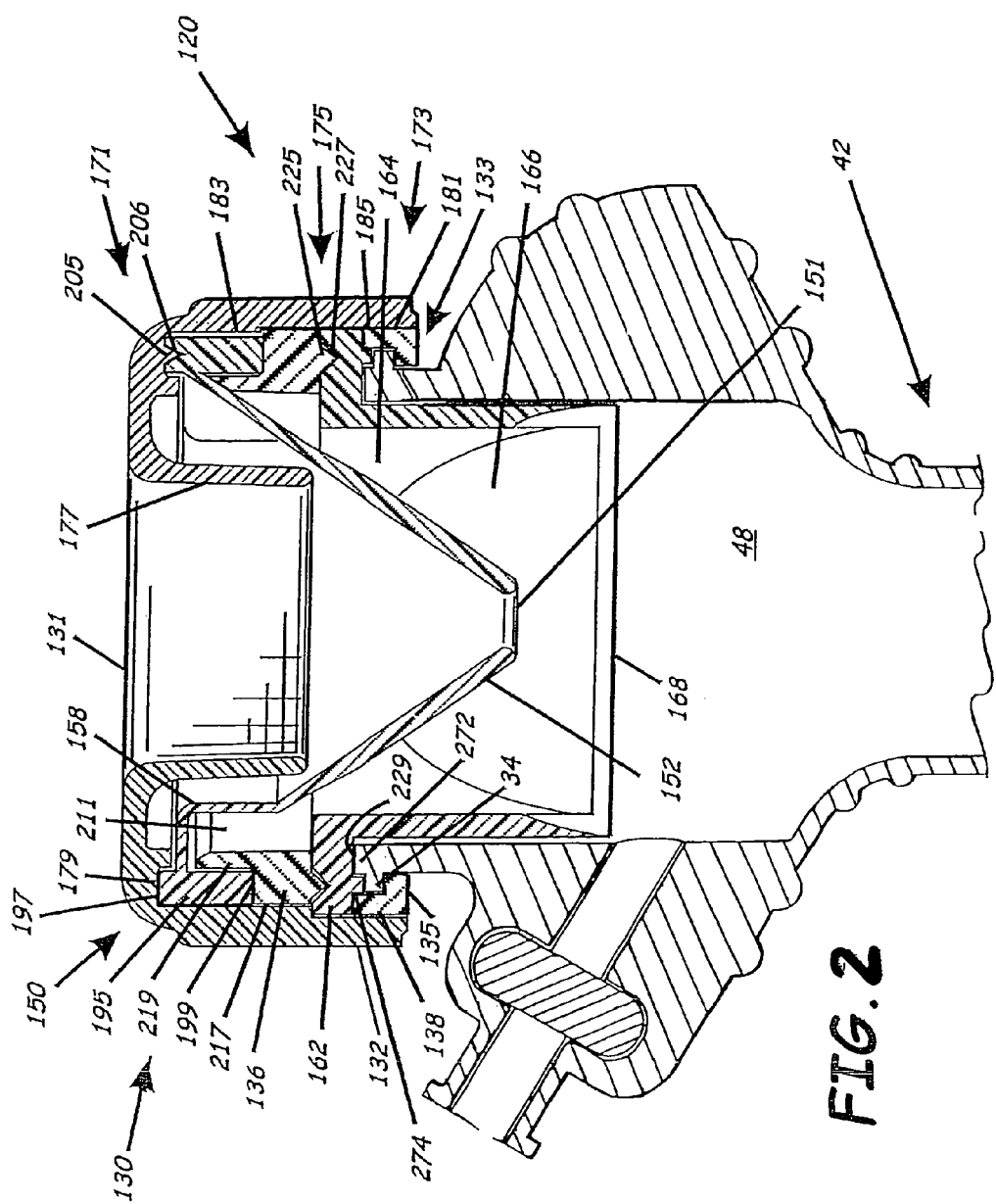
FIG. 2 is a fragmentary sectional view of an exemplary trocar system having first and second valves taken along line 1-1 of FIG. 1.
Figures 3, 4:
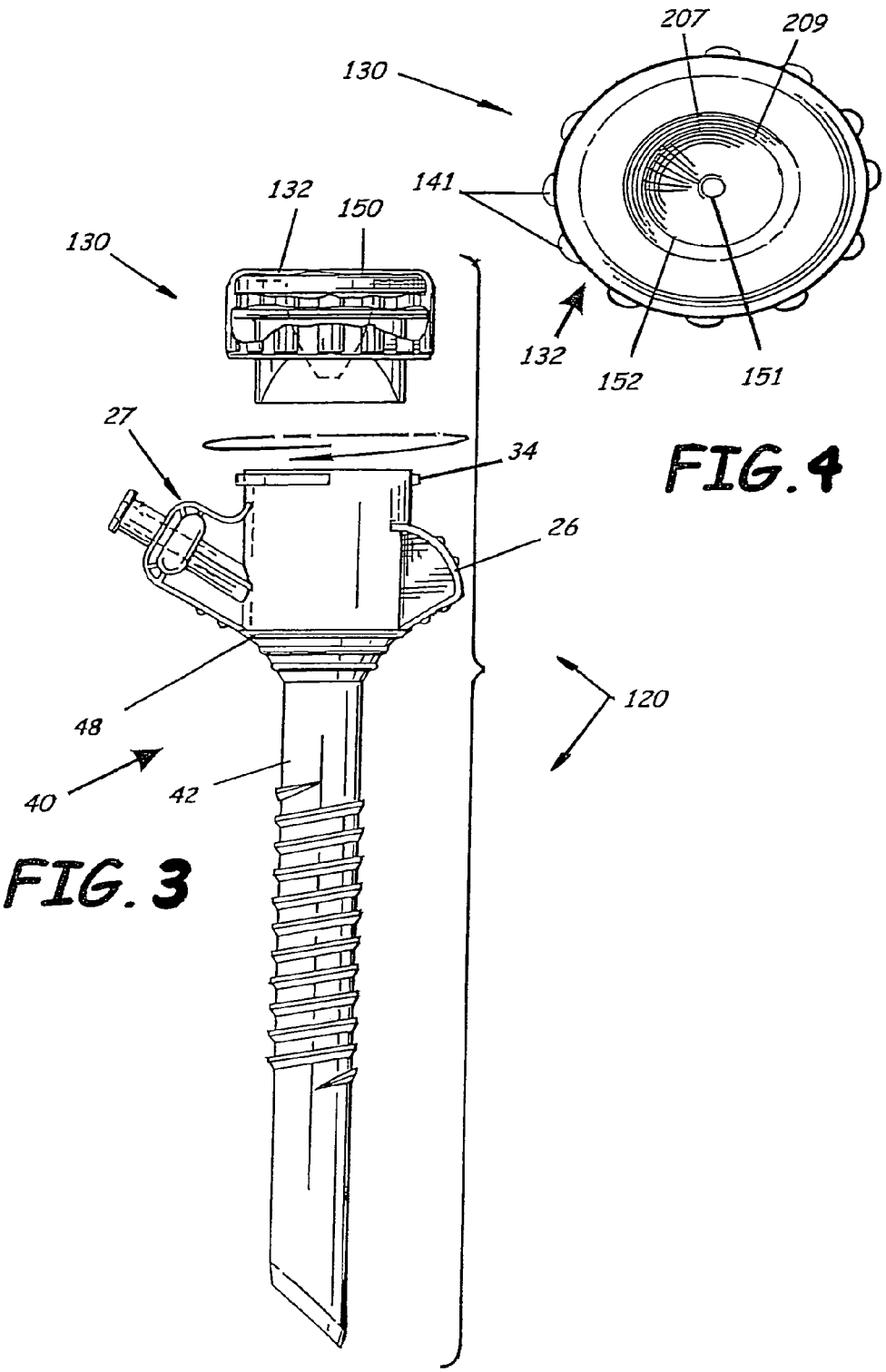
FIG. 3 is a side elevational view of an exemplary trocar system.
FIG. 4 is a top plan view of a cap assembly of an exemplary trocar system.

Cap assembly 130 of trocar system 120 includes valve housing 132, which can have, for example, a substantially annular shape, can include proximal end housing portion 171, distal end housing portion 173, and medial housing portion 175 connected to and extending therebetween, as shown in FIG. 2. Proximal end housing portion 171 can include first opening 131 having a first opening diameter defined by portions of inner valve housing sidewall 177 extending distally in a substantially axial direction. Inner valve housing sidewall 177 forming first opening 131 extends substantially axially downward toward valve opening 151 of valve 150, described below. Upper portion of first opening 131 can be rounded so as not to have any right angle edges at first opening 131, but with the resulting cross-section forming substantially cylindrical first opening 131 extending along the same axis as that for valve opening 151. Proximal end housing portion 171 can also include annular valve ring recess 179 for retaining valve 150. Distal end housing portion 173 can include second opening 133 having a second opening diameter defined by distal valve housing sidewall 181 extending in a substantially axial direction. Medial housing portion 175 can include first proximal valve housing inner perimeter surface 183 and second distal valve housing inner perimeter surface 185 which can have a perimeter size or circumference the same or slightly larger than that of first proximal valve housing inner perimeter surface 183.

Figure 5:
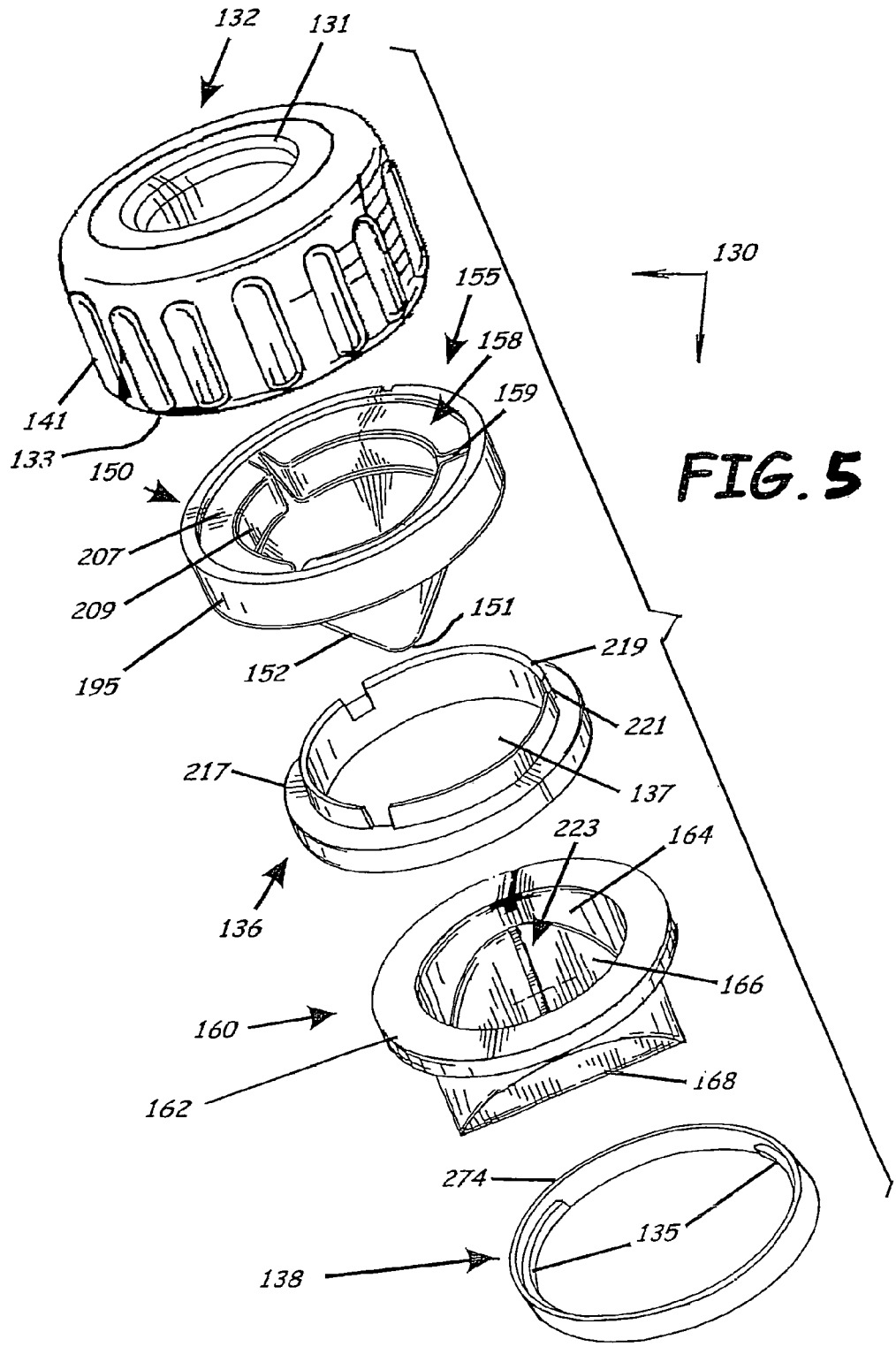
FIG. 5 is an exploded view of a cap assembly of an exemplary trocar system.
Figure 6:
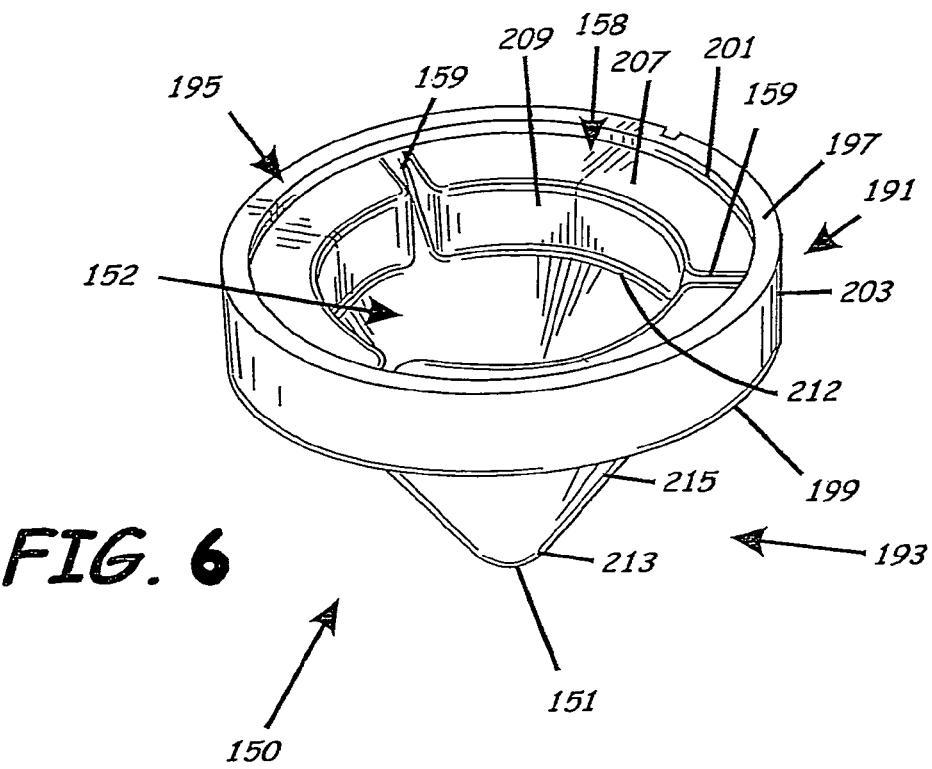
FIG. 6 is a perspective view of a valve of an exemplary trocar system.
Figure 7:
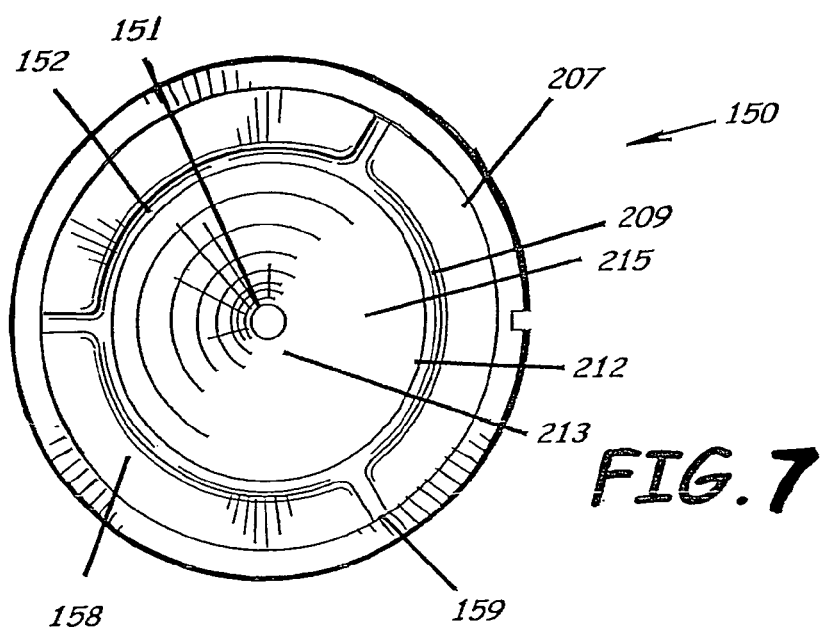
FIG. 7 is a top plan view of a valve of an exemplary trocar system.
Figure 8:
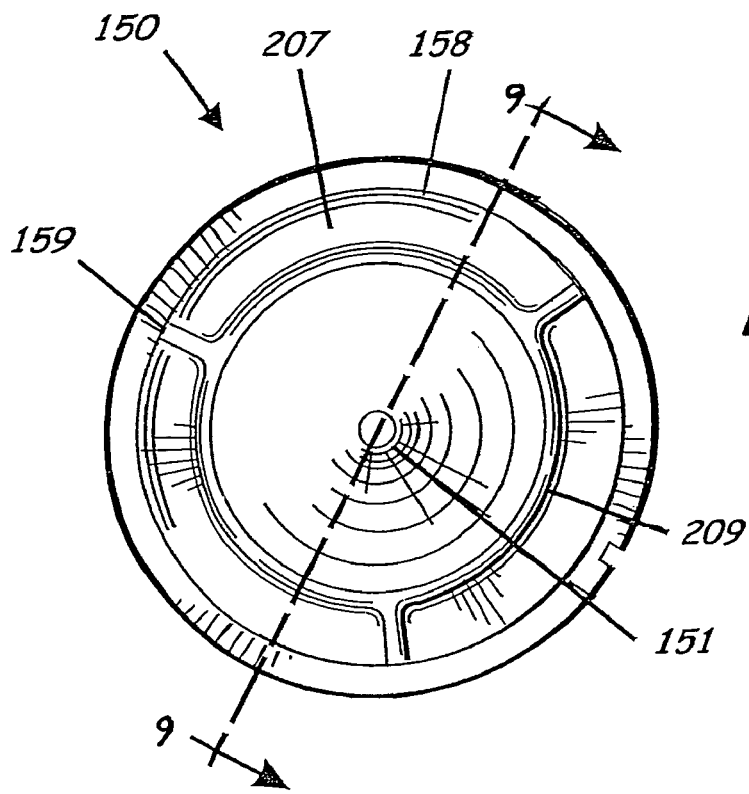
FIG. 8 is a bottom plan view of a valve of an exemplary trocar system.
Figure 9:
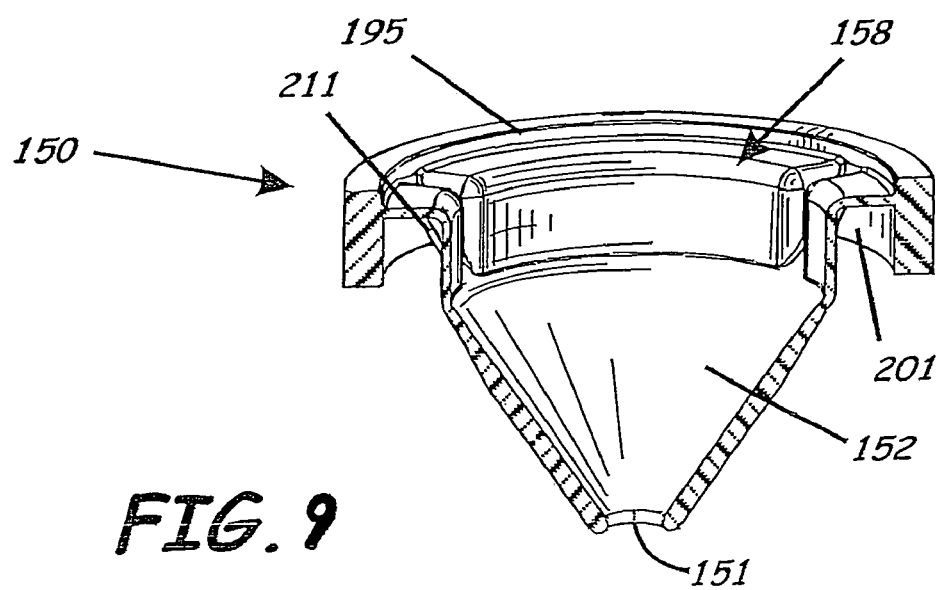
FIG. 9 is sectional view of a valve of an exemplary trocar system taken along line 9-9 of FIG. 8.
Figure 10:
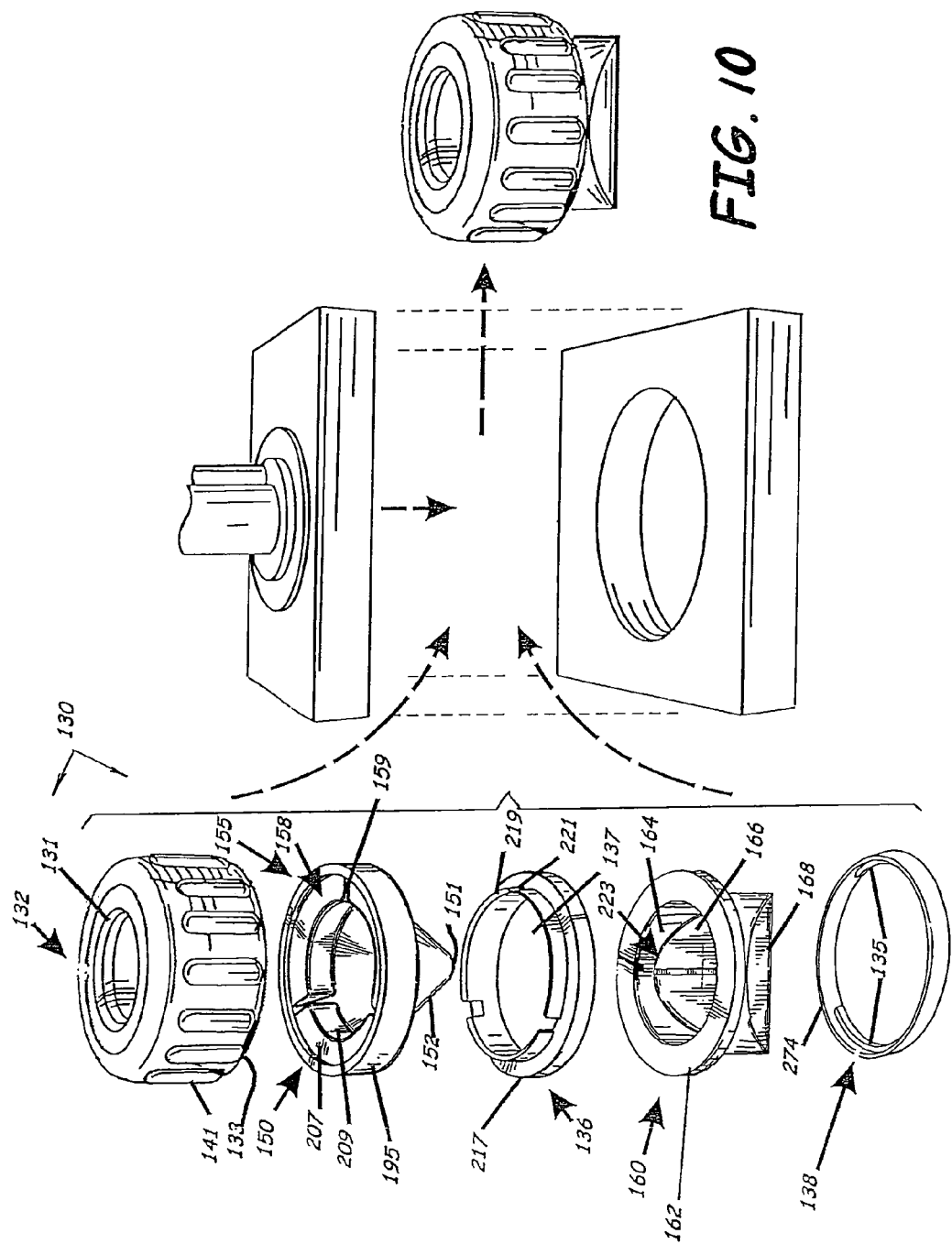
FIG. 10 is an environmental perspective view of an exemplary valve, valve mold, and a slab illustrating the formation of a valve.
Figure 11:
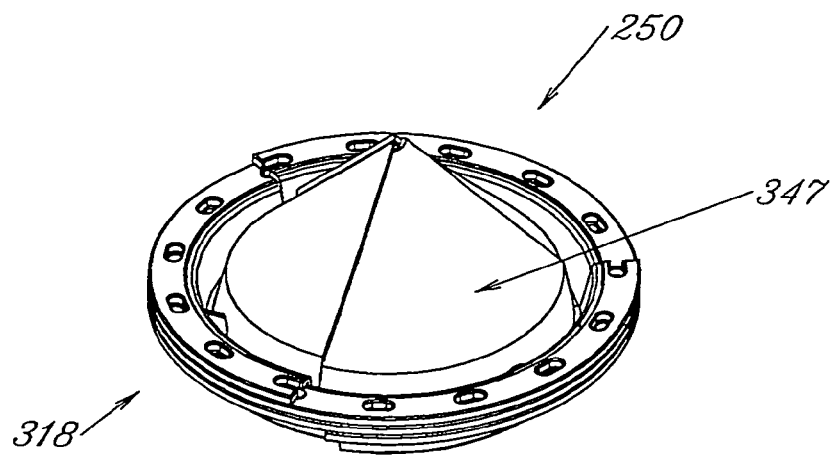
FIG. 11 is a side perspective view of a sealing gland according to an embodiment of the present invention.

As shown in FIG. 5, exemplary valve 150 can include valve body 155 positioned at least partially within valve housing 132, axially aligned with first opening 131 of valve housing 132, wherein valve body 155 includes proximal valve section 191 fixedly positioned entirely within valve housing 132 and distal valve section 193 extending axially from proximal valve section 191. Proximal valve section 191 includes valve ring 195 positioned in valve ring recess 179 (FIG. 2) of valve housing 132. Valve ring 195 has proximal surface 197, distal surface 199, inner perimeter surface 201, and outer perimeter surface 203 defining an outer perimeter of valve body 155. Proximal valve section 191 also can include plurality of convolutes 158 each having first sidewall 207 extending radially inwardly from a portion of inner perimeter surface 201 of valve ring 195 and second sidewall 209 extending axially from first sidewall 207 substantially parallel to or slightly angled from inner perimeter surface 201 of valve ring 195 and forming an inner radial periphery of proximal valve section 191. Inner perimeter surface 201 of valve ring 195, first sidewall 207, and second sidewall 209 of each of plurality of convolutes 158 form a respective convolute recess 211. Proximal valve section 191 can also include a plurality of rib members 159 (see, e.g., FIG. 5), each radially extending substantially an entire distance between the inner radial periphery of proximal valve section 191 and inner perimeter surface 201 of valve ring 195 and symmetrically positioned spaced-apart from each other.

Distal valve section 193 can extend axially from proximal valve section 191 and can include valve extension 152 extending axially from plurality of convolutes 158. Valve extension 152 can have proximal end portion 212 substantially connected to a distal portion of each of the plurality of convolutes 158, distal end portion 213, and medial portion 215 connected to and extending therebetween. According to an embodiment of valve extension 152, medial portion 215 can have a substantially frustro-conical or other similar conical-form shape, as illustrated. Distal valve section 193 includes valve opening 151 positioned in distal end portion 213 of valve extension 152, which can have, for example, an annular shape. Valve opening 151 is adapted to individually and separately receive therethrough any one of the plurality of different elongate tools 22, 23, 24, 25, each having a different diameter so that when any one of the plurality of elongate tools is positioned through valve opening 151, a septum-type seal is maintained between peripheries of distal end portion 213 of valve extension 152 surrounding valve opening 151 and outer peripheries of any one of the plurality of elongate tools when extending therethrough. As noted previously, plurality of tools 22, 23, 24, 25 each have an elongate body for extending through valve housing 132, valve opening 151 of valve 150, and cannula 40.

Plurality of convolutes 158 are each positioned between and connected to any two adjacent rib members 159. According to an embodiment of convolutes 158, each convolute 158 can be in a selected biased position before and after each of the plurality of different elongate tools, individually and separately, extends through valve opening 151. According to an embodiment of the present invention, the combination of convolutes 158 and valve extension 152 allow for axial movement of tools 22, 23, 24, 25, without a corresponding movement within valve opening 151 with respect to outer peripheries of the tools. Valve body 155, in general, and the portion of valve extension 152 surrounding opening 151, in particular, can be formed of a flexible material to provide the elastic range necessary to accommodate plurality of elongate tools 22, 23, 24, 25.

Cap assembly 130 can also include compression ring 136 positioned in valve housing 132 at a medially axial position between first and second openings 131, 133, of valve housing 132, abuttingly contacting axially facing distal surface 199 of valve ring 195. Compression ring 136 includes compression ring opening 137 substantially aligned axially with first opening 131 of valve housing 132 to allow extension of the plurality of elongate tools therethrough. Compression ring opening 137 can also be sized to allow at least portions of inner valve housing sidewall 177 and valve 150 to extend therethrough. Compression ring 136 also includes outer perimeter surface 217 having a radial diameter sized so that compression ring 136 substantially abuttingly contacts the proximal valve housing inner perimeter surface 183 when positioned within valve housing 132, and includes annular flange 219 extending into each one of the plurality of convolute recesses 211.

Compression ring 136 is positioned to compress valve ring 195 against an axially facing inner surface and an axially facing shoulder of proximal end housing portion 171 of valve housing 132 which, together along with a portion of first proximal valve housing inner perimeter surface 183 of medial housing portion 175, form valve ring recess 179, and/or to compress valve ring 195 against first proximal valve housing inner perimeter surface 183 of medial housing portion 175, to hold valve ring 195 in valve ring recess 179 to fixedly position valve 150 within valve housing 132. That is, compression ring 136 is positioned so that proximal valve housing inner perimeter surface 183, surfaces forming valve ring recess 179, and annular flange 219 of compression ring 136 rigidly hold valve ring 195 within valve housing 132.

Annular flange 219 of compression ring 136 can include plurality of notches 221 symmetrically positioned spaced-apart from each other so that each of notches 221 aligns with and receives a separate one of plurality of rib members 159 to thereby rotationally align compression ring 136 with valve ring 195 when positioned in contact therewith. Alternatively, annular flange 219 can include a plurality of separate spaced apart flanges (not shown) having a gap between each pair of flanges defining notch 221 and aligned with plurality of remembers 159 to thereby enhance positioning of valve ring 195. To further enhance positioning of valve ring 195, according to an embodiment of valve housing 132 and valve ring 195, the axially facing inner surface of proximal end housing portion 171 of valve housing 132 can include one or more protuberances 205 extending at least partially along the length of valve ring recess 179, and proximal surface 197 of valve ring 195 can include one or more recesses 206 or can deform to form recess 206, as illustrated, to receive one or more protuberances 205 to thereby enhance positioning of valve ring 195 within valve housing 132.

Cap assembly 130 can also include second valve 160. Second valve 160 is advantageously positioned adjacent second opening 133 of valve housing 132, abuttingly contacting compression ring 139. Second valve 160 advantageously has annular flange portion 162 spaced axially from the valve ring of first valve 150. Annular flange portion 162 can have a radial diameter sized so that annular flange portion 162 substantially abuttingly contacts distal valve inner housing perimeter surface 185 and axially facing distal surface of compression ring 136 adjacent compression ring opening 137 to enhance the positioning of second valve 160 within valve housing 132. Second valve 160 includes second valve opening 223 positioned within annular flange portion 162 and, when positioned within valve housing 132, is substantially aligned axially with first and second openings 131, 133, of valve housing 132 to allow extension of plurality of elongate tools 22, 23, 24, 25, therethrough.

Annular-shaped sidewalls 164 are connected to annular flange portion 162 and extend distally in a substantially axial direction when positioned in valve housing 132. At least one pair of valve flaps 166 is connected to and extends inwardly from sidewalls 164 and flange portion 162. Sidewalls 164, for example, can extend distally of the end of valve housing 132 so that flange portion 162 retains only portions of valve 160 within valve housing 132 and yet slidably or in a spaced-apart relation have other portions which are positioned within proximal portion 48 of cannula body 42. Similarly, portions of valve extension 152 and/or valve opening 151 of first valve 150 can extend within proximal portion 48 of cannula body 42. Pair of valve flaps 166 has at least one opening or slit 168 along common peripheral edges thereof through which tools 22, 23, 24, 25 can individually and separately extend. Second valve 160 also advantageously can have ribs or rib members (not shown), e.g., formed integrally therewith as a single piece, and connected to sidewalls 164 to reduce drag, as will be understood by those skilled in the art. Second valve 160 can also be advantageously impregnated with a lubricant such as an oil material to enhance performance of the valve.

Proximal surface of annular flange portion 162 of second valve 160 can include an at least partially annular recess 227 or can deform to form recess 227, as illustrated, to receive an at least partially annular protuberance 225 extending from a distal surface of compression ring 136 to thereby enhance positioning of second valve 160 at least partially within valve housing 132. A distal surface of annular flange portion 162 of second valve 160 can further include second valve annular-shaped recess 229 adapted to receive axially extending annular-shaped flange 272 of maximal portion 48 of cannula 40 to thereby enhance positioning of at least part of proximal portion 48 of cannula 40 within valve housing 132.

Cap assembly 130 can also include cap seal ring 138 positioned at least partially within valve housing 132 and having axially extending flange 274 positioned to abuttingly contact a distal surface of annular flange portion 162 of second valve 160 when positioned in valve housing 132. Cap seal ring 138 can include plurality of radially extending flanges 135, each adapted to engage outer peripheries of a separate one of the plurality of radially extending flanges 34 of cannula 40 to slidably detachably connect valve housing 132 to cannula 40. Cannula 40 can also include an annular shaped axially extending flange adapted to engage annular-shaped recess 229 of second valve 160 to thereby enhance positioning of cannula 40 securely against second valve 160 when positioned in engagement with radially extending flanges 135 of cap seal ring 138.

Therefore, according to the present invention, and with reference to the preferred use thereof in with such trocar system 120 as is described hereinabove, as shown in FIGS. 10-28, the preferred embodiment of the present invention employs a variable opening flexible valve or sealing gland 250, 250', which can be used with cannula 40 as a substitute for valve 150 with little modification to cap assembly 130 to allow positioning in valve (seal gland) housing 132. As indicated hereinabove, for simplicity, components common to both the exemplary trocar system 120 described with reference to FIGS. 1-10 such as cannula 40, and the preferred incorporated use of the present invention that will be described will retain their original numbering. Those components not common will be renumbered accordingly. Further, the following discussion of sealing gland 250 (see, e.g., FIGS. 11-15) and sealing gland 250' (see, e.g., FIGS. 22-25) will primarily refer to sealing gland 250 for simplicity. The differences between sealing gland 250 and sealing gland 250' will be described later. Items common to both sealing gland 250 and sealing gland 250' will retain the same numerical identifiers.

According to an embodiment of the present invention, sealing gland 250 can include a plurality of valve body sections 255 (see, e.g., FIGS. 12 and 15-19). Valve body sections 255 can include a silicon material coated with paralene to enhance flexibility and/or include others known to those skilled in the art. As perhaps best shown in FIGS. 16 and 17, each valve body section 255 has first valve section 291 including annular shaped valve ring 295, second valve section 293 extending from first valve section 291 and including valve extension 252 having proximal end portion 312, distal end portion 313, and substantially conically shaped medial portion 315 connected to and extending therebetween. Valve opening 251 in distal end portion 313 of valve extension 252 is adapted to receive therethrough an elongate tool such as, for example, tools 22, 23, 24, 25 (see, e.g., FIG. 1). Slit 316 in each valve body section 255 can extend between valve opening 251 and valve ring 295, completely separating valve body section 255 in valve ring 295.

Figure 15:
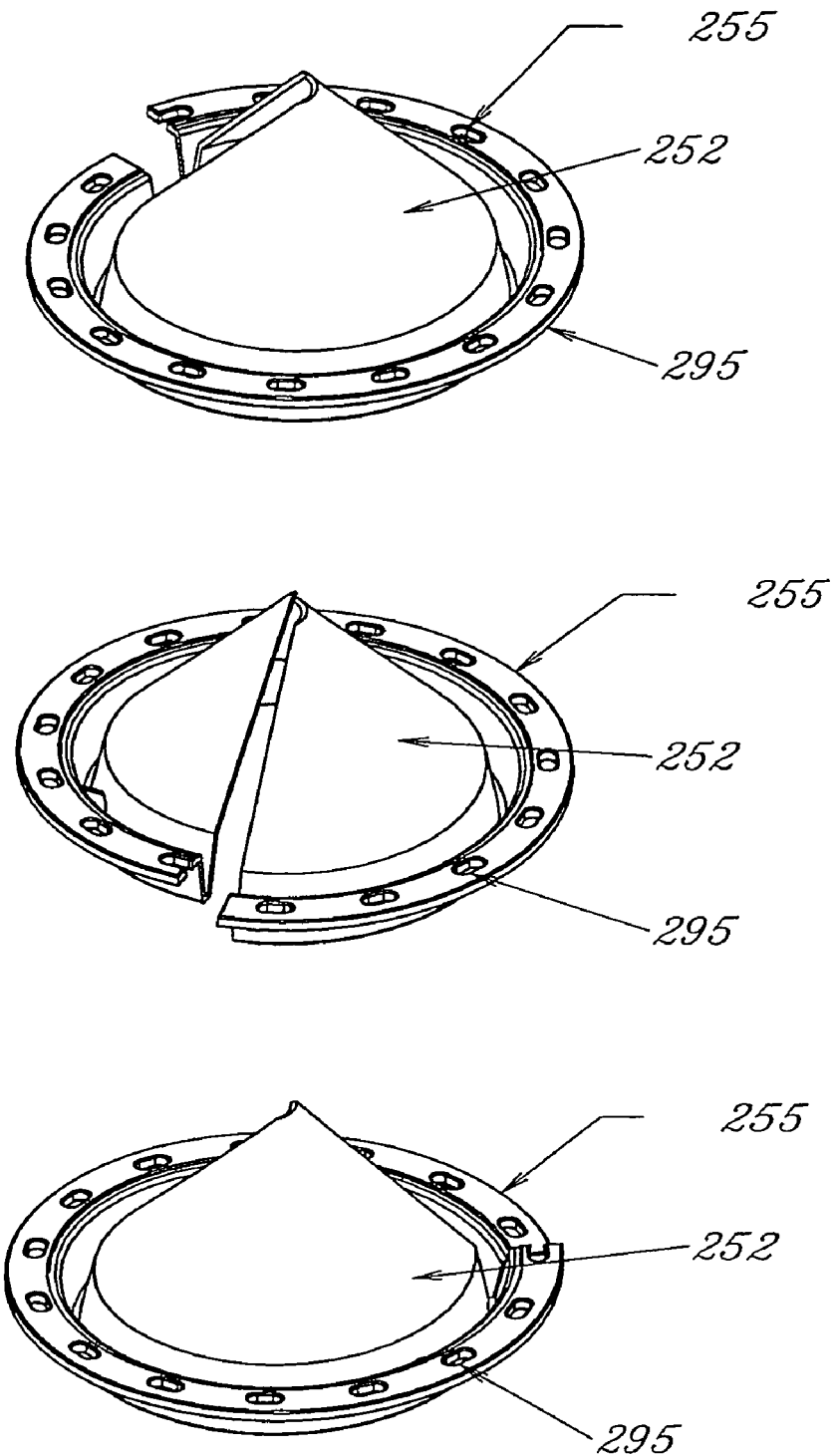
FIG. 15 is an exploded view of a sealing gland comprising three slitted valves according to an embodiment of the present invention.
Figure 17:
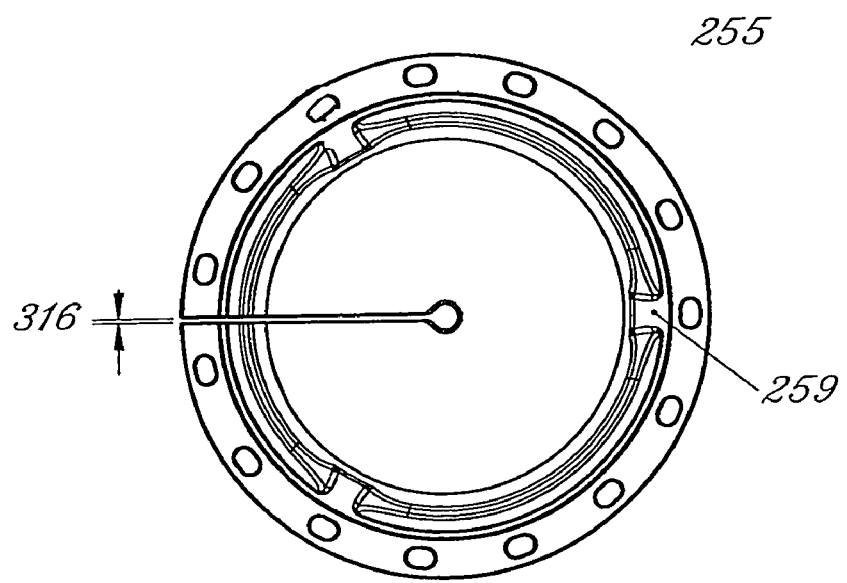
FIG. 17 is a top plan view of a slitted valve according to an embodiment of the present invention.
Figure 18:
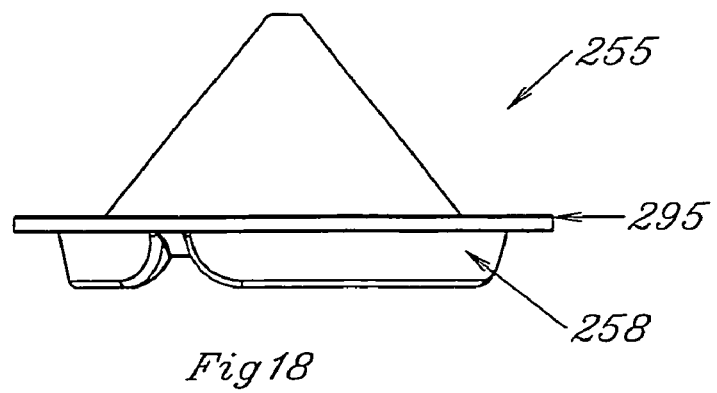
FIG. 18 is a side elevational view of a slitted valve according to an embodiment of the present invention.
Figure 19:
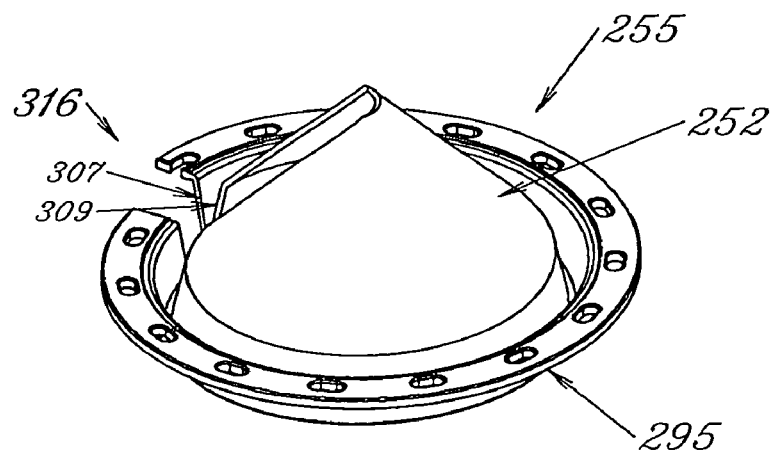
FIG. 19 is a perspective view of a slitted valve having a deformed shape according to an embodiment of the present invention.

In an embodiment of the present invention, such as that shown FIG. 17, slit 316 is aligned with the longitudinal axis of valve body section 255. In another embodiment of the present invention (not shown), the portion of slit 316 extending through valve ring 295 is arcuate, angled, or otherwise shaped to enhance interface within valve housing 132. FIG. 19 shows single valve body section 255 deformed to enhance interweaving with other valve body sections 255 and illustrating the extent of slit 316. FIG. 15 illustrates three valve body sections 255 deformed to allow interweaving of valve body sections 255, deforming the seal gland shown in FIGS. 11-14.

Figure 12:
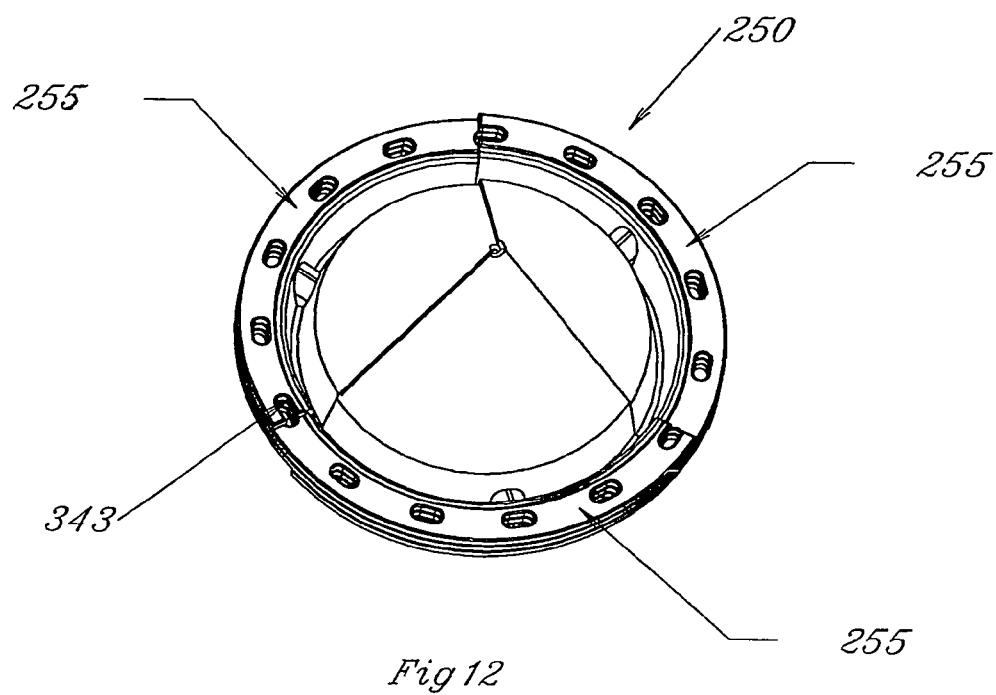
FIG. 12 is a top perspective view of a sealing gland according to an embodiment of the present invention.
Figure 13:
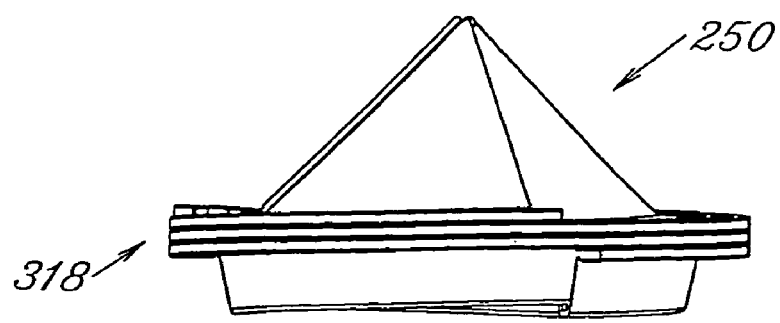
FIG. 13 is a side elevational view of a sealing gland according to an embodiment of the present invention.
Figure 14:
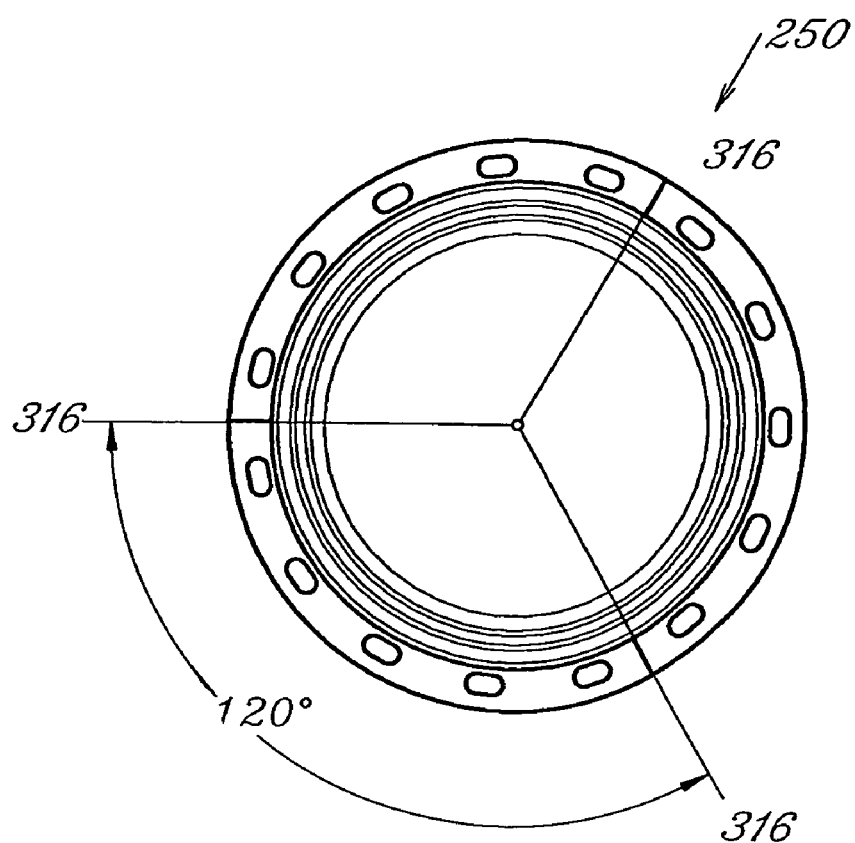
FIG. 14 is a top plan view of a sealing gland illustrating symmetrical spacing of the slits in three valves according to an embodiment of the present invention.

As perhaps best shown in FIGS. 12 and 15, for the exemplary sealing gland 250 including three valve body sections 255, each of the valve rings 295 of each of the valve body sections 255 abuttingly contact one or both of the other of the valve rings 295 along their proximal and distal facing surfaces. This interweaving of valve rings 295 forms a layered cap assembly valve ring 318, as perhaps best illustrated in FIGS. 11 and 13.

Figure 29:
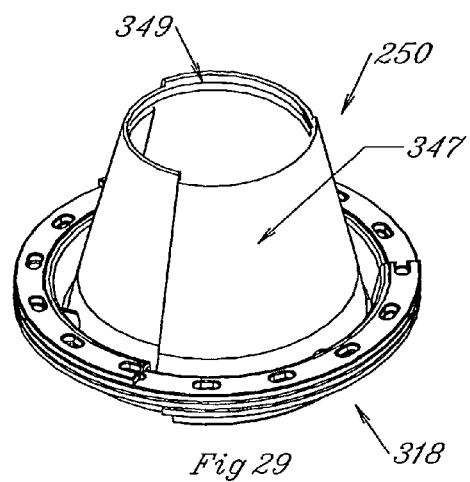
FIG. 29 is a top perspective view of a sealing gland showing a maximum stage opening according to an embodiment of the present invention.

Similarly, medial portion 315 of valve extension 252 of each one of valve body sections 255 are interweaved. As perhaps best shown in FIG. 14, valve body sections 255 can be positioned so that slits 316 are evenly spaced. In this illustrated example utilizing three valve body sections 255, slits 316 are spaced 120 degrees apart. Valve extensions 252, however, rather than being securely connected, are in sliding contact with valve extension 252 of one or both of the other valve body sections 255 to form an interweaved valve extension 347. That is, as perhaps best shown sequentially in FIGS. 26-29, the combination of valve body sections 255 form a substantially conically shaped iris diaphragm portion of sealing gland 250 which can flexibly adjust the size of iris 349 between the closed position (FIG. 26) and the fully open position (FIG. 29). Although not shown in FIGS. 26-29, expansion of the size of iris 349 is in response to insertion of a tool such as, for example, tool 22, 23, 24, 25. Beneficially, such conical iris-type design allows sealing gland 250 to be flexible and deformable, thus allowing the center opening of iris 349 to move laterally without loss of sealing when a medical instrument or tool is inserted through cannula 40.

Figure 24:
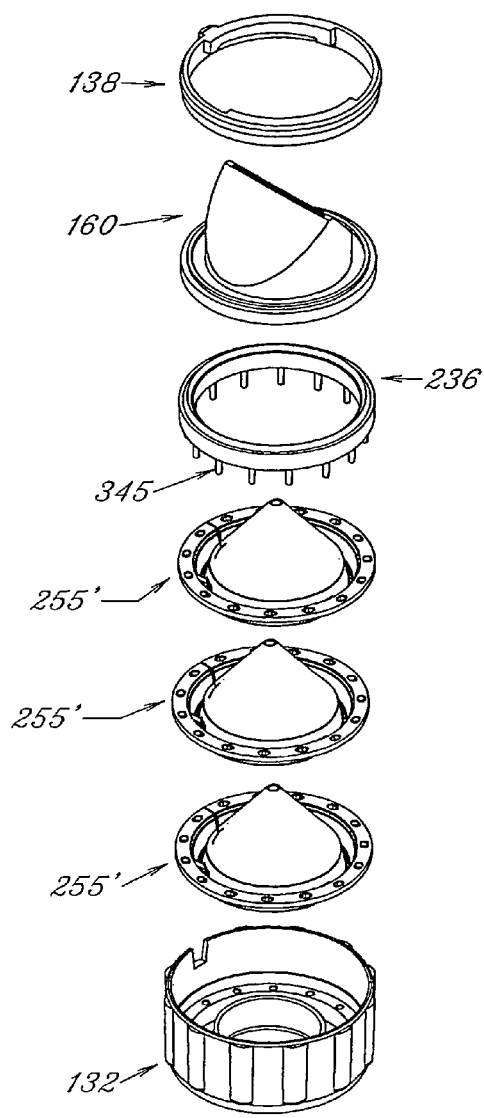
FIG. 24 is an exploded view of a cap assembly of a trocar system according to an embodiment of the present invention.
Figure 25:
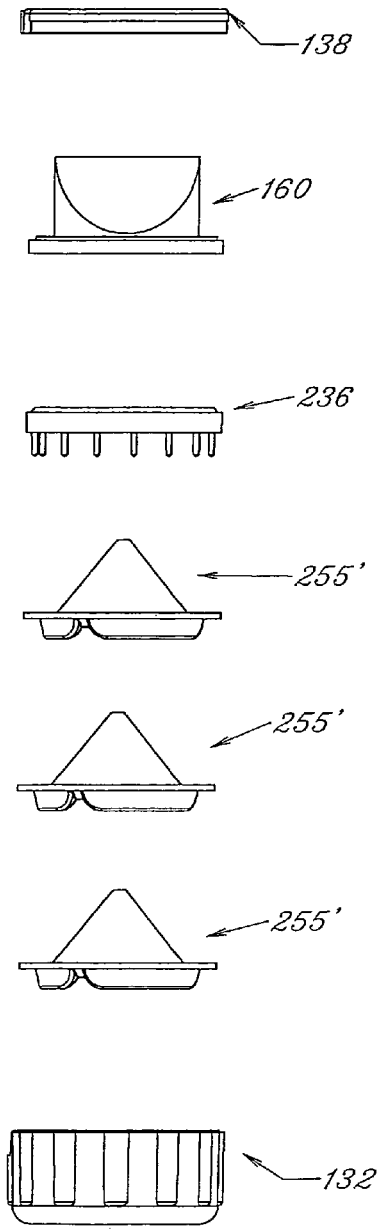
FIG. 25 is an exploded view of a cap assembly of a trocar system according to an embodiment of the present invention.
Figure 26:
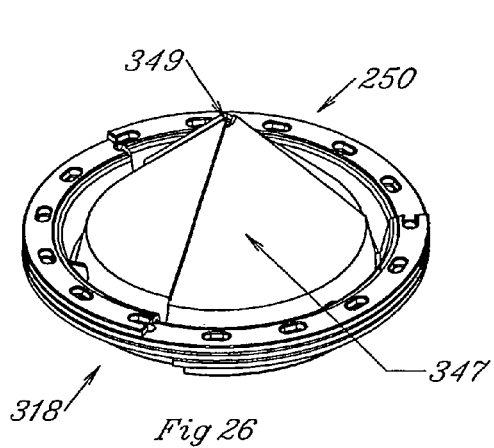
FIG. 26 is a top perspective view of a sealing gland showing a closed stage opening according to an embodiment of the present invention.
Figure 27:
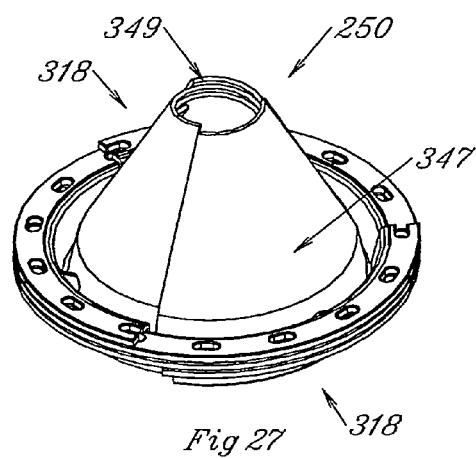
FIG. 27 is a top perspective view of a sealing gland showing a first stage opening according to an embodiment of the present invention.
Figure 28:
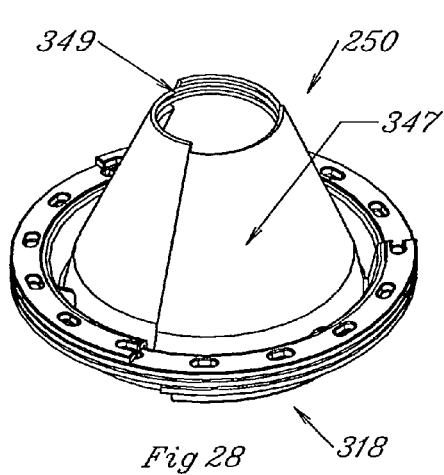
FIG. 28 is a top perspective view of a sealing gland showing a medium stage opening according to an embodiment of the present invention.

As perhaps best shown in FIGS. 12 and 24, according to the exemplary embodiment of the present invention, valve rings 295 can include a plurality of spaced apart recesses 343 extending through the proximal or distal surfaces. According to an embodiment of the present invention, to enhance interweaving of the valve body sections 255, at least a portion of the recesses 345 of each valve ring 295 can receive ultraviolet bonding agent. Further, to enhance movement yet provide stability, layered cap assembly valve ring 318 is clamped between distal facing surfaces 179 and inner perimeter surface 183 of housing 132 by compression ring 236 (see FIGS. 24-25) to immobilize cap assembly valve ring 318, and still allow interweaved valve extension 347 and iris 349 to have lateral and radial movement. Compression ring 236 includes a plurality of spaced apart pins 345 extending proximate a surface. Correspondingly, recesses 343 are positioned to receive plurality of spaced apart pins 345 to thereby further immobilize valve ring 295 of each one of valve body sections 255, 255' with respect to valve ring 295 of each other of the plurality of valve body sections 255, 255'.

Figure 16:
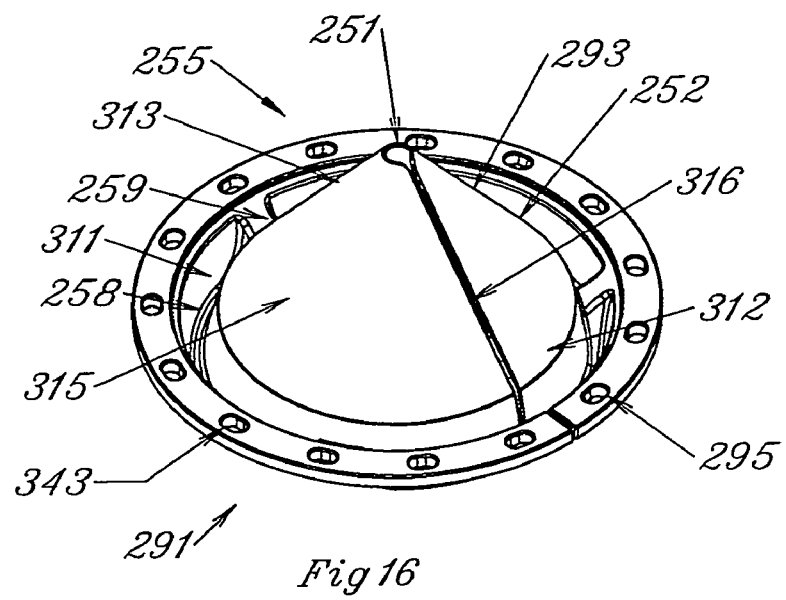
FIG. 16 is a perspective view of a slitted valve according to an embodiment of the present invention.

As perhaps best shown in FIGS. 16 and 17, according to embodiments of sealing gland 250 having valve body sections 255, proximal end portion 312 of second valve section 293 of each of valve body sections 255 includes plurality of convolutes 258, e.g., three, each having first sidewall 307 (best illustrated in FIG. 19) extending radially inwardly from a portion of the inner perimeter surface of valve ring 295 and second sidewall 309 extending axially from first sidewall 307 and forming an inner radial periphery of proximal end portion 312 of second valve section 293. The inner perimeter surface of valve ring 295, first sidewall 307, and second sidewall 309 of each convolute 258 form a respective convolute recess 311 for each convolute 258. The plurality of convolutes 258 are biased so that distal end portion 313 of the respective valve extension 252 is substantially inline with a central axis of a bore of valve/seal gland housing 132, 132' (see, e.g., FIGS. 2, 22, 23) without imparting a significant transverse force when an elongate tool is extended through the iris 349.

Each of the convolutes 258 for each proximal end portion of the second valve section of each of the plurality of valve body sections 255 can be positioned between and connected to two adjacent rib members 259 (perhaps best illustrated in FIG. 17). Rib members 259 can function to reinforce movement and deformation recovery of convolutes 258 so that iris 349 formed by valve openings 251 of each of the valve body sections 255 can move transverse to the longitudinal axis of the valve without loss of sealing when an elongate tool is positioned therethrough.

Figure 20:
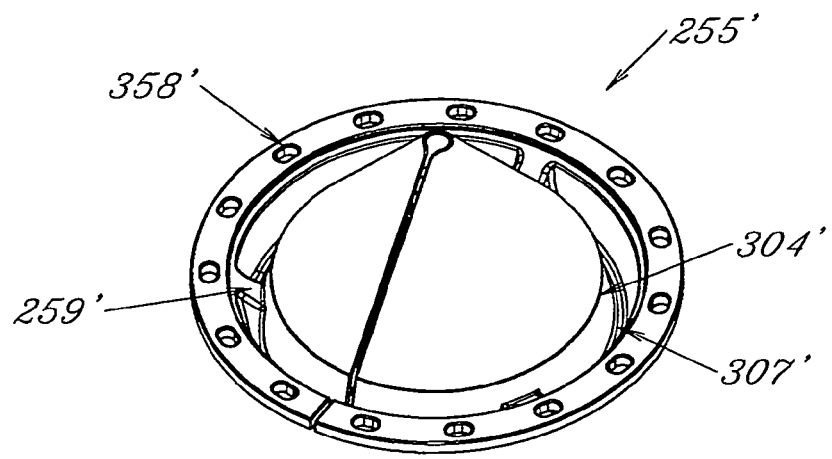
FIG. 20 is a perspective view of a slitted valve according to an embodiment of the present invention.
Figure 21:
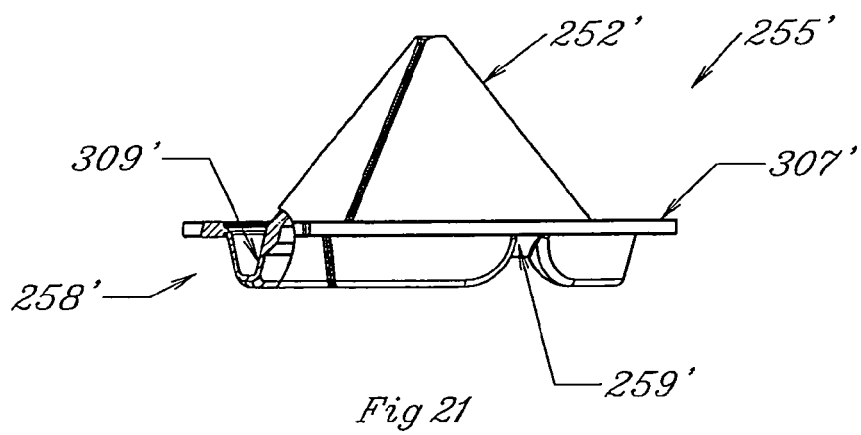
FIG. 21 is a side elevational view of a slitted valve according to an embodiment of the present invention.
Figure 22:
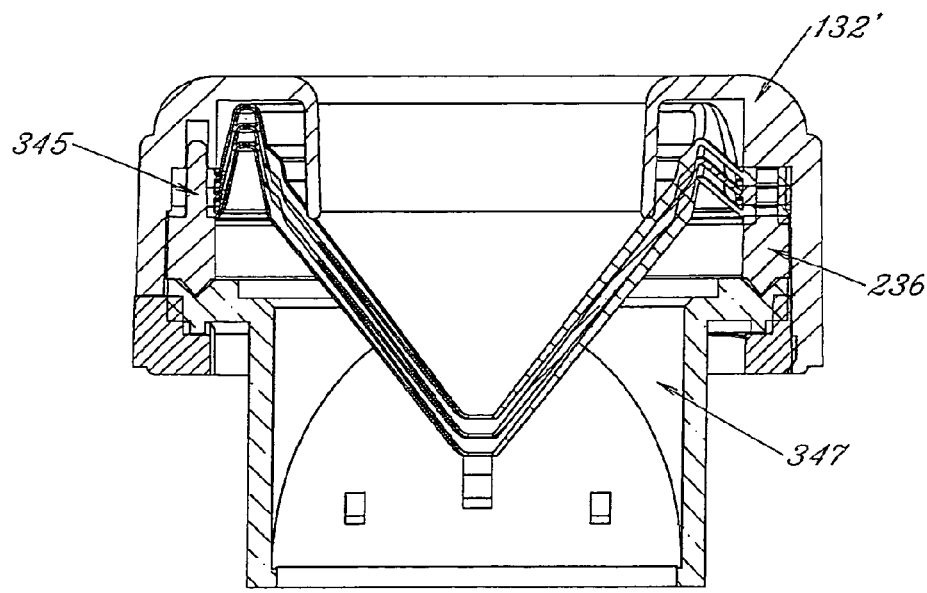
FIG. 22 is a fragmentary perspective view of a cap assembly according to an embodiment of the present invention.
Figure 23:
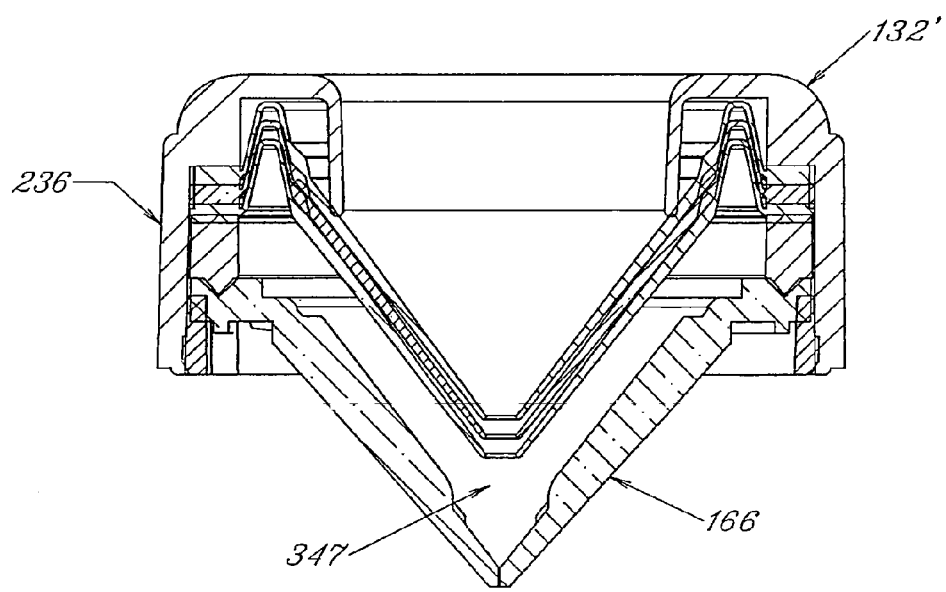
FIG. 23 is a fragmentary perspective view of a cap assembly taken along the 23-23 line of FIG. 22 according to an embodiment of the present invention.

As perhaps best shown in FIGS. 20-21, according to embodiments of sealing gland 250', the proximal end portion of the second valve section of each of the plurality of valve body sections 255' includes a plurality of radial extensions 258', each having first sidewall 307' extending radially inwardly from a portion of the inner perimeter surface of valve ring 295 and second sidewall 309' extending axially from first sidewall 307 approximately parallel to the inner perimeter surface of sealing gland housing 132' (see, e.g., FIGS. 22-25) and forming an inner radial periphery of the proximal end portion of the second valve section. Plurality of radial extensions 258' are biased so that the distal end portion of the respective valve extension 252' is substantially in-line with a central axis of a bore of sealing gland housing 132' without imparting a significant transverse force when an elongate tool is extended through the iris 349.

To add further support to the valve extension 252', the proximal end portion of the second valve section of each of the plurality of valve body sections 255' each can include a plurality of rib members 259', each radially extending substantially an entire distance between the inner radial periphery of the proximal end portion of the second valve section and the inner perimeter surface of the valve ring 295 and, for example, symmetrically positioned spaced-apart from each other, e.g., 120 degrees in this illustration. The plurality of rib members 259' are positioned to bias valve extension 252' of each valve body section 255' so that the distal end portion of the respective valve extension 252' is substantially in-line with a central axis of a bore of sealing gland housing 132'.

Embodiments of the present invention also include a method of forming sealing gland 250, 250', for a cap assembly of cannula 40. For example, according to an embodiment of the present invention, the method can include forming plurality of valve body sections 255, 255', each having a first valve section including annular shaped valve ring 295, a second valve section extending from the first valve section and including valve extension 252, 252', having a proximal end portion, a distal end portion, and a substantially conically shaped medial portion connected to and extending therebetween. Valve opening 251 can be positioned in the distal end portion of valve extension 252, 252', and is adapted to receive therethrough an elongate tool.

The method also includes forming slit 316 in the each of the plurality of valve body sections 255, 255', extending between the respective valve opening 251 and the respective valve ring 295, and positioning each one of valve rings 295 of each of valve body sections 255, 255', in abutting contact with the other valve rings 295 to form layered cap assembly valve ring 318. The medial portion of valve extension 252, 252', of each one of valve body sections 255, 255', slidably contacting the medial portion of valve extension 252, 252', of the other valve body sections 255, 255', to form interweaved cap assembly valve extension 347. The combination of valve body sections 255, 255' form sealing gland 250, 250'.

According to an embodiment of the present invention, valve ring 295 of each of the plurality of valve body sections 255, 255, includes plurality of spaced apart recesses 343 extending longitudinally through valve ring 295. As such, the method can further include the step of clamping sealing gland 250, 250' between the sealing gland housing (see, e.g., FIGS. 22 and 23) and compression ring to 36 having a corresponding plurality of spaced apart pins 345 positioned to extend through the plurality of spaced apart recesses 343 to immobilize valve ring 295 while allowing at least portions of valve extension 252, 252' to remain laterally movable.

In the drawings and specification, there have been disclosed a typical preferred embodiment of the invention, and although specific terms are employed, the terms are used in descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That claimed is:

1. A variable opening flexible sealing gland for a cap assembly of a cannula comprising:
    a plurality of valve body sections, each having
        a first valve section including an annular shaped valve ring, said first valve section being discontinuous, having at least one complete separation defined in said annular shaped valve ring,
        a second valve section extending from the first valve section and including a valve extension having a proximal end portion, a distal end portion, and a substantially conically shaped medial portion connected to and extending therebetween, said second valve section being discontinuous, having at least one complete separation defined in said valve extension,
        a valve opening positioned in the distal end portion of the valve extension and adapted to receive therethrough an elongate tool, and
        a slit extending between the valve opening and the valve ring, said slit formed by a combination of said at least one complete separation of said first valve section and said at least one complete separation of said second valve section, and said slit extending through said valve ring,
    each one of the valve rings of each of the plurality of valve body sections abuttingly contacting at least one other of the valve rings of the plurality of valve body sections to form a layered cap assembly valve ring,
    the medial portion of the valve extension of each one of the plurality of valve body sections slidably contacting the medial portion of the valve extension of at least one other of the plurality of valve body sections, and
    the combination of the plurality of valve body sections forming a substantially conically shaped iris diaphragm portion of the sealing gland.

2. A sealing gland as defined in claim 1, wherein each one of the valve rings of each of the plurality of valve body sections abuttingly interlockingly contact at least two other of the valve rings of the plurality of valve body sections to form the layered cap assembly valve ring.

3. A sealing gland as defined in claim 2, wherein the valve ring of each of the plurality of valve body sections includes a first surface and a second surface longitudinally positioned opposite the first surface, the valve ring including a plurality of spaced apart recesses extending between the first surface and the second surface and positioned to receive a plurality of pins extending from a proximal surface of a compression ring to thereby immobilize the valve ring of each one of the plurality of valve body sections with respect to the valve ring of each other of the plurality of valve body sections.

4. A sealing gland as defined in claim 1, wherein the slit of each one of the plurality of valve body sections is approximately evenly positioned spaced apart from the slit of each other of the plurality of valve body sections.

5. A sealing gland as defined in claim 1, wherein the valve ring of each of the plurality of valve body sections includes an inner perimeter surface, and wherein the proximal end portion of the second valve section of each of the plurality of valve body sections includes an inner radial periphery and a plurality of rib members each radially extending substantially an entire distance between the inner radial periphery of the proximal end portion of the second valve section and the inner perimeter surface of the valve ring and symmetrically positioned spaced-apart from each other.

6. A sealing gland as defined in claim 5, wherein the plurality of rib members of the proximal end portion of the second valve section of each of the plurality of valve body sections are positioned to bias the valve extension so that the distal end portion of the respective valve extension is substantially in-line with a central axis of a bore of an associated sealing gland housing.

7. A sealing gland as defined in claim 1, wherein the valve ring of each of the plurality of valve body sections includes an inner perimeter surface, and wherein the proximal end portion of the second valve section of each of the plurality of valve body sections includes a plurality of radial extensions each having a first sidewall extending radially inwardly from a portion of the inner perimeter surface of the valve ring and a second sidewall extending axially from the first sidewall and forming an inner radial periphery of the proximal end portion of the second valve section, the plurality of radial extensions biased so that the distal end portion of the respective valve extension is substantially in-line with a central axis of a bore of an associated sealing gland housing without imparting a significant transverse force when an elongate tool is extended through an aperture formed by the valve openings of each of the plurality of valve body sections.

8. A sealing gland as defined in claim 1, wherein the valve ring of each of the plurality of valve body sections includes an inner perimeter surface, and wherein the proximal end portion of the second valve section of each of the plurality of valve body sections includes a plurality of convolutes each having a first sidewall extending radially inwardly from a portion of the inner perimeter surface of the valve ring and a second sidewall extending axially from the first sidewall and forming an inner radial periphery of the proximal end portion of the second valve section, the inner perimeter surface of the valve ring, the first sidewall, and the second sidewall of each of the plurality of convolutes forming a respective convolute recess for each respective one of the plurality of convolutes.

9. A sealing gland as defined in claim 8, having a longitudinal axis, and wherein each of the plurality of convolutes for each proximal end portion of the second valve section of each of the plurality of valve body sections are positioned between and connected to two adjacent rib members, the rib members reinforcing movement and deformation recovery of the convolutes so that an aperture formed by the valve openings of each of the plurality of valve body sections can move transverse to the longitudinal axis of the valve without loss of sealing when the elongate tool is positioned therethrough.

10. A sealing gland as defined in claim 8, wherein the plurality of convolutes of the proximal end portion of the second valve section of each of the plurality of valve body sections are biased so that the distal end portion of the respective valve extension is substantially in-line with a central axis of a bore of an associated sealing gland without imparting a significant transverse force when an elongate tool is extended through an aperture formed by the valve openings of each of the plurality of valve body sections.

* * * * *